(12) United States Patent
Källander et al.

(10) Patent No.: US 7,488,577 B2
(45) Date of Patent: Feb. 10, 2009

(54) METHOD FOR MEASURING DNA POLYMERIZATION AND APPLICATIONS OF THE METHOD

(75) Inventors: Clas Källander, Uppsala (SE); Ingvar Pettersson, Uppsala (SE); Simon Gronowitz, Uppsala (SE); Xingwu Shao, Uppsala (SE)

(73) Assignee: Cavidi Tech AB, Uppsala (SE)

( * ) Notice: Subject to any disclaimer, the term of this patent is extended or adjusted under 35 U.S.C. 154(b) by 348 days.

(21) Appl. No.: 10/479,510

(22) PCT Filed: Jun. 14, 2002

(86) PCT No.: PCT/SE02/01155

§ 371 (c)(1),
(2), (4) Date: Dec. 10, 2003

(87) PCT Pub. No.: WO02/103039

PCT Pub. Date: Dec. 27, 2002

(65) Prior Publication Data

US 2004/0157230 A1    Aug. 12, 2004

Related U.S. Application Data

(60) Provisional application No. 60/297,773, filed on Jun. 14, 2001.

(51) Int. Cl.
*C12Q 1/68*  (2006.01)
*C12P 19/34* (2006.01)
*C07H 21/02* (2006.01)
*C07H 21/04* (2006.01)

(52) U.S. Cl. .................. 435/6; 435/91.1; 435/91.2; 536/23.1; 536/24.3; 536/24.33

(58) Field of Classification Search ............... None
See application file for complete search history.

(56) References Cited

FOREIGN PATENT DOCUMENTS

WO    WO 90/06373    *    6/1990
WO    0101129 A2        1/2001

OTHER PUBLICATIONS

Portsman et al., "A sensitive non-isotopic assay specific for HIV-1 associated reverse transcriptase," Journal of Virological Methods, 1991, vol. 31, pp. 181-188.*
Rytting et al., "Monoclonal Antibodies to Native HIV Type 1 Reverse Transcriptase and Their Interaction with Enzymes from Different Subtypes," Aids Research and Human Retroviruses, 2000, vol. 16, No. 13, pp. 1281-1294.*

* cited by examiner

*Primary Examiner*—Young J Kim
(74) *Attorney, Agent, or Firm*—Bacon & Thomas, PLLC

(57) ABSTRACT

A method for measuring DNA-dependent DNA polymerisation in a biological sample, is described. The method comprises the steps of providing a primer with a single stranded short specific sequence, which is unable to base pair internally, bound to a solid phase; contacting the primer construct with a reaction mixture containing a single stranded deoxynucleotide template with a part of the sequence complementary to the primer and the four deoxynucleoside triphosphates, one of which is modified so that it is specifically recognized by a labeled antibody; adding a biological sample comprising the DNA polymerase, such as retrovirus reverse transcriptase (RT), to the mixture; allowing the polymerase reaction to proceed; incubating the immobilized reaction product with the labeled antibody; detecting the amount of bound labeled antibody; and measuring the amount of incorporated modified deoxynucleoside triphosphate, as a measure of the DNA polymerisation, which may be used drug susceptibility testing. A commercial package is also disclosed.

14 Claims, 5 Drawing Sheets

METHOD FOR MEASURING DNA POLYMERIZATION AND APPLICATIONS OF THE METHOD

Figure 1:
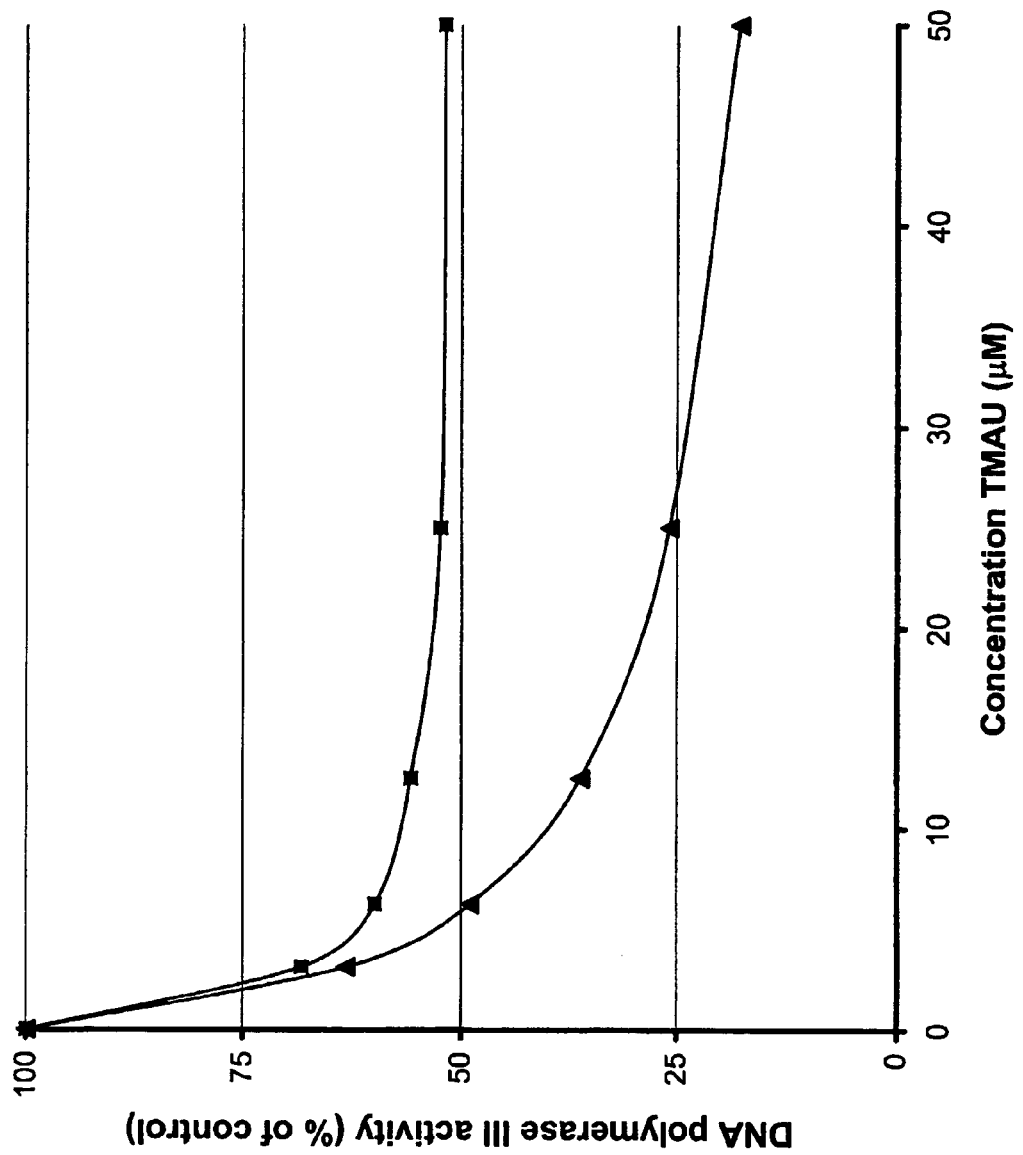

This application is the National Phase Application of PCT?SE02/01155 filed Jun. 14, 2002, which claims benefit under 35 U.S.C. 119(e) of U.S. Provisional Application Ser. No. 60/297,773, filed Jun. 14, 2001.

The present invention relates to a method for measuring DNA polymerization and applications of the method. More precisely, the invention relates to a method for measuring DNA-dependent DNA polymerization.

BACKGROUND

The latest decades have experienced a rapid development of new methods for measurement of reverse transcription, RNA dependent DNA polymerization. The more complex issue concerning methods for quantification of DNA dependent DNA polymerization has so far received much less attention.

The classic DNA polymerase activity assays involve use of DNAse treated DNA ("activated DNA") as primer/template and incorporation of radiolabeled nucleotides into DNA (Aposhian and Kornberg 1962). Measurement of acid preciptable radioactivity allows calculation of the amount of nucleotides incorporated and the number of enzyme units present. However, use of radioactivity is currently restricted and discouraged in many laboratories and there is due to this a general trend away from radioactivity-based techniques.

For DNA polymerases a commercial assay based on ELISA detection of digoxigenine labeled nucleotides incorporated in newly made DNA is available (Roche Molecular Biochemicals Cat. no 1468120, U.S. Pat. No. 5,635,350). This assay is hampered by the use of two different nucleotide substrate analogues with bulky groups, digoxigenine as label and biotin for product immobilization. As a result the polymerization reaction velocity and subsequent detection sensitivity is reduced. The utilization of substrate analogues with highly deviating kinetic properties makes this system less relevant for studies of drug susceptibility of different polymerases.

Another more attractive alternative method is a fluorescence-based assay for DNA polymerase holoenzyme, based on the specific reaction of the dye PicoGreen with double-stranded DNA (Seville et all 1996). The latter process has recently been modified to make it suitable for a broader range of different DNA polymerizing enzymes (Tveit and Kristensen 2001). This assay is technically simple and based on the utilization of natural nucleotides. The detection sensitivity is, however, still in the same range as the classic radioactive DNA polymerase assay and the applications described demonstrates a detection range of 0.05-0.5 U DNA polymerase/sample.

HIV therapy today is based on multidrug therapy. The regimens are based on combinations of all three types of drugs available: nucleoside analogues, non-nucleoside analogues and protease inhibitors. The strategy is to minimize the probability for a mutant virus to survive.

The reverse transcriptase (RT) inhibitors are either nucleoside analogues or non-nucleoside analogues. The non-nucleoside inhibitors bind to a hydrophobic pocket in the RT enzyme close to, but not contiguous with, the active site. HIV-1 replication is inhibited allosterically by displacing the catalytic aspartate residues relative to the polymerase binding site.

The nucleoside inhibitors used today terminates the DNA chain elongation as they lack a 3'-hydroxyl group. Prolonged therapy with nucleoside inhibitors commonly leads to the development of resistant virus. This process is associated with the gradual appearance of mutations in the virus pol gene, each leading to defined amino acid substitutions (for a review see Vandamme et al 1998). The effects of these substitutions at the enzymatic levels is complicated and includes enhancement of a primitive DNA editing function. This reaction is nucleotide dependent and produces dinucleoside polyphosphate and an extendible DNA 3' end (Arion et al 1998, Meyer et al 1999).

The HIV-1 RT as well as other reverse transcriptases perform three different enzymatic reactions: RNA-dependent DNA polymerization, DNA-dependent DNA polymerization, and degradation of RNA in the DNA-RNA hybrid (RNase H). The HIV reverse transcriptase, encoded by the pol gene, is a heterodimer consisting of a p66 and a p51 subunit. Both RNA-dependent DNA polymerization and DNA-dependent DNA polymerization are performed by the same active site localized in the p66 subunit (for a review see Goff 1990). The reaction mechanism of these drugs has mainly been defined according to their action on the RNA-dependent DNA polymerization reaction. The effect on the DNA-dependent DNA polymerization reaction is comparatively less studied.

Provided that the reaction mechanism and the active metabolized drug is known and available, phenotypic virus drug susceptibility could be determined at the enzyme level. Depending on the capacity of the enzyme assays and the virus isolation techniques used, the drug sensitivity testing can theoretically be done either on supernatants from virus culture propagation, the primary virus isolation or on virus preparations recovered directly from the patients. Conventional RT activity assay is performed by utilizing an artificial template-primer construction and labeled deoxynucleoside triphosphate as nucleotide substrate. The template/primer pair poly(rA)/oligo(dT) is the most efficient and most used combination for determination of HIV as well as for other retroviral RTs. A drawback of this type of assay when drug sensitivity testing is concerned, is that only non-nucleoside analogues or analogues that can base pair with rA can be tested. Analogues to the other nucleotide bases will require an assay based on a variable polymer template. RNA polymers containing pyrimidine bases are notoriously sensitive to RNases and in practice not compatible with biological samples. It would therefore be advantageous to base a polymerase assay intended for drug sensitivity testing on a variable DNA template, provided that the assay system gives results that correlate with those from inhibition of reverse transcription and classic phenotypic drug resistance tests.

HIV therapy used today is only one example of the potency of DNA polymerase inhibitors. The current situation concerning resistance development among bacteria and other microorganisms motivates the search for new classes of antimicrobial drugs. DNA polymerases are one of the major targets during this effort. As such there is a great demand for technically simple polymerase assays, which do not cause potential environmental hazards and can be applied for drug screening towards a broad range of microbial DNA polymerase isozymes. The toxicity of the drug leads found must further be evaluated towards the corresponding mammalian DNA polymerases.

Quantification of proliferation associated polymerases such as polymerase-α and -δ can be used for monitoring cell proliferation. It may be mentioned in this context that the serum levels of thymidine kinase, another cell proliferation associated enzyme, are currently used for prognosis and classification of malignant disease (U.S. Pat. No. 4,637,977). Phosphorylation of thymidine is just one of the two intracellular synthetic pathways, which provides thymidine triphosphate for DNA synthesis. Measurement of the DNA polymerase itself has the potential to give a more correct estimation of total DNA synthesis compared to thymidine kinase activity or thymidine incorporation.

DESCRIPTION OF THE INVENTION

The present invention provides a non-radioactive DNA polymerase assay in microtiter plate format enabling colorimetric or fluorimetric product detection.

In a preferred embodiment it utilizes, as nucleoside triphosphate substrate, 5-bromodeoxyuridine 5'-triphosphate (BrdUTP). The difference in Van der Waals' radius between the 5' position bromine in BrdUTP and the 5' position methyl group in thymidine triphosphate is minimal (1.95 A compared to 2.0 A) and the enzyme kinetic properties of these two nucleotides are quite similar. The method can be aromatized and have a detection range down to 3 nU polymerase activity/sample.

One of the applications of the present invention is drug susceptibility testing. All anti-retroviral drugs approved hitherto interfere with the enzymatic reaction of either the viral protease or the RT. There are in addition candidate drugs in the pipeline which affect the function of the retroviral integrase.

In particular, the present invention provides a procedure to measure a broad range of different DNA-dependent DNA polymerases. It has proved suitable even for studies of highly processive DNA polymerase systems in spite of the comparatively short template used. The usefulness for determination of the activity of bacterial polymerase I and III, mammalian DNA polymerase $\alpha$, $\beta$ and $\gamma$, a proliferation associated polymerase activity in human serum and DNA dependent DNA polymerization by HIV RT is demonstrated, but the method can be used for studies of virtually all viral and cellular DNA polymerases. One of the features that distinguish the present. DNA polymerase assay from previous art is its outstanding sensitivity, which makes detection of down to 3 nU $E.\ coli$ DNA polymerase I activity feasible.

Thus, one aspect of the invention is directed to a method for measuring DNA dependent DNA polymerisation in a biological sample, comprising the steps of
 a) providing a primer with a single stranded short specific sequence, which is unable to base pair internally, bound to a solid phase,
 b) contacting the primer construct with a reaction mixture containing a single stranded deoxy nucleotide template with a part of the sequence complementary to the primer and the four deoxy nucleoside triphosphates, one of which is modified so that it is specifically recognized by a labeled antibody,
 c) adding a biological sample comprising the DNA polymerase to the mixture of b),
 d) allowing the polymerase reaction to proceed,
 e) incubating the immobilized reaction product resulting from d) with the labeled antibody,
 f) detecting the amount of bound labeled antibody with the aid of the label used, and
 g) measuring the amount of incorporated modified deoxynucleotide, as a measure of the DNA polymerization, with the aid of the label of the bound antibody.

In an embodiment the DNA polymerization is made by a retrovirus reverse transcriptase (RT), such as human immunodeficiency virus (HIV) RT.

In another embodiment the modified deoxy nucleoside triphosphate is 5-bromodeoxyuridine 5'-triphosphate (BrdUTP) and the labeled antibody is an alkaline phosphatase (Ap) conjugated anti-BrdU monoclonal antibody.

In a preferred embodiment of the method according to the invention, the measured DNA polymerisation is used for drug susceptibility testing.

The drug susceptibility testing is performed to evaluate if a certain drug is effective in a mammalian individual, and the result may be used for selecting drug treatment therapy for that individual. In practice, the individual will be subjected to testing at several points of time to monitor the development of drug treatment in said individual.

The invention is also directed to a commercial package comprising written and/or data carrier instructions for measuring DNA-dependent DNA polymerisation according the invention. The package will comprise at least the following items:
 a) a primer with a single stranded short specific sequence, which is unable to base pair internally, bound to a solid phase,
 b) a single stranded deoxynucleotide template with a part of the sequence complementary to the primer in a),
 c) the four deoxynucleoside triphosphates, one of which is modified so that it is specifically recognized by a labeled antibody, and
 d) the labelled antibody that recognizes the modified deoxynucleoside triphosphate in c).

The invention will now be illustrated by the following unlimiting description of embodiments and drawings of the invention.

The teachings of the cited literature is incorporated herein by reference.

SHORT DESCRIPTIONS OF THE DRAWINGS

FIG. 1. demonstrates the effects of variation in template sequence on inhibition of DNA polymerase III with TMAU.

Figure 2:
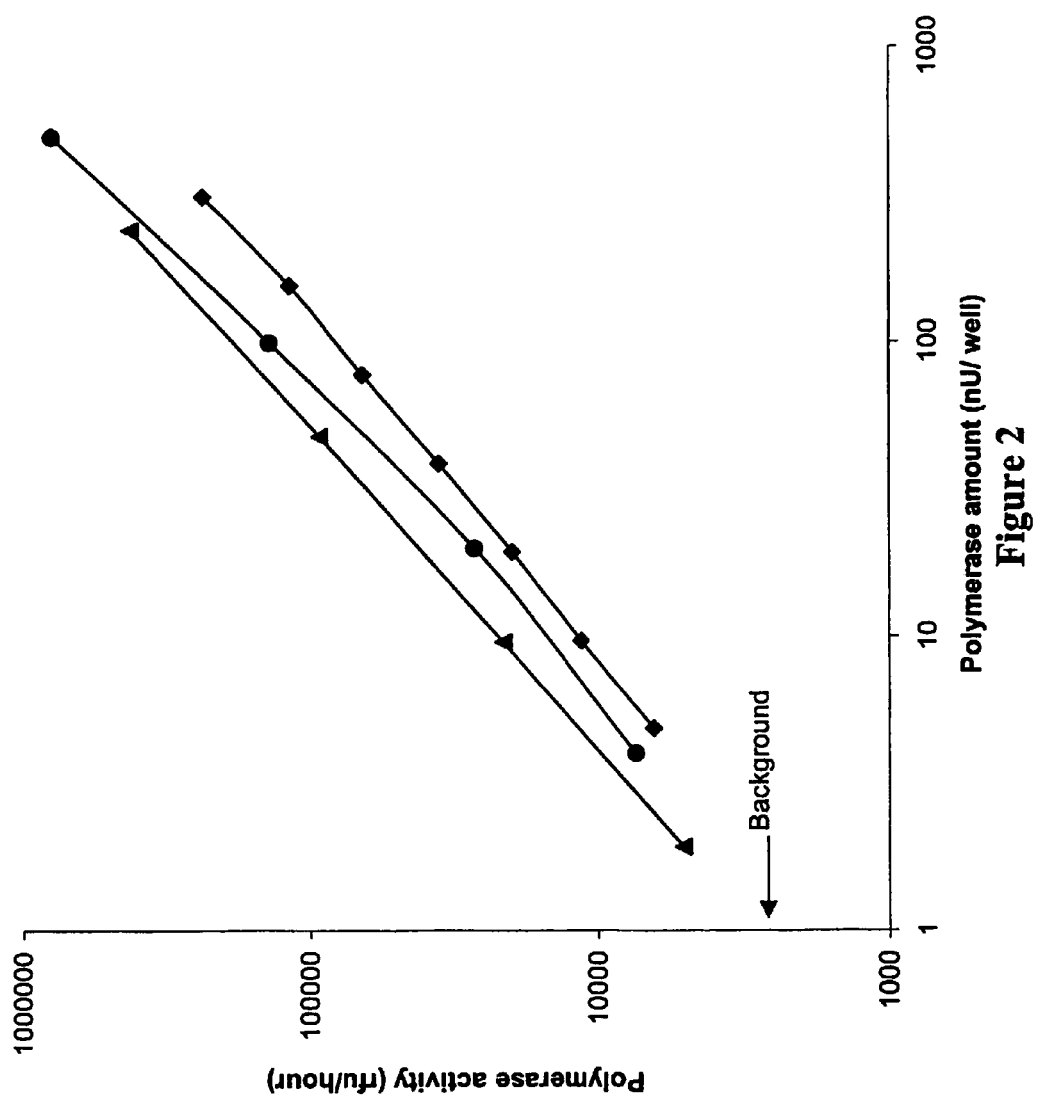

FIG. 2. exemplifies the detection sensitivity of the DNA polymerase assay. HIV-1 wild type RT (♦), mammalian DNA polymerase β (●) and $E.\ coli$ DNA polymerase I (▲).

Figure 3:
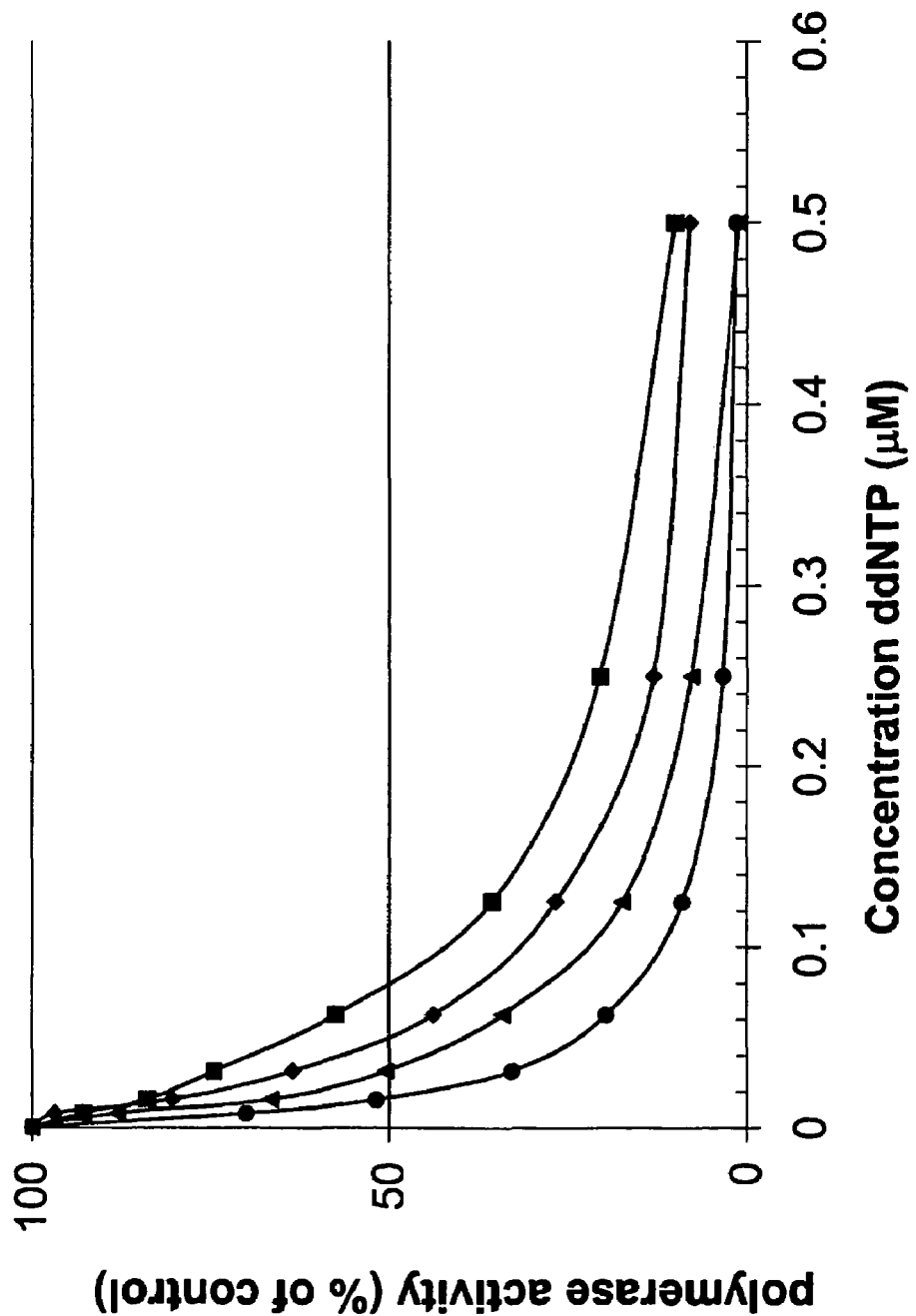

FIG. 3. demonstrates the ability of the DNA polymerase assay to measure inhibition by the dideoxy analogues to all the four DNA bases. Symbols: ddATP (■), ddGT (♦), ddCTP (●) and ddTP (▲).

Figure 4:
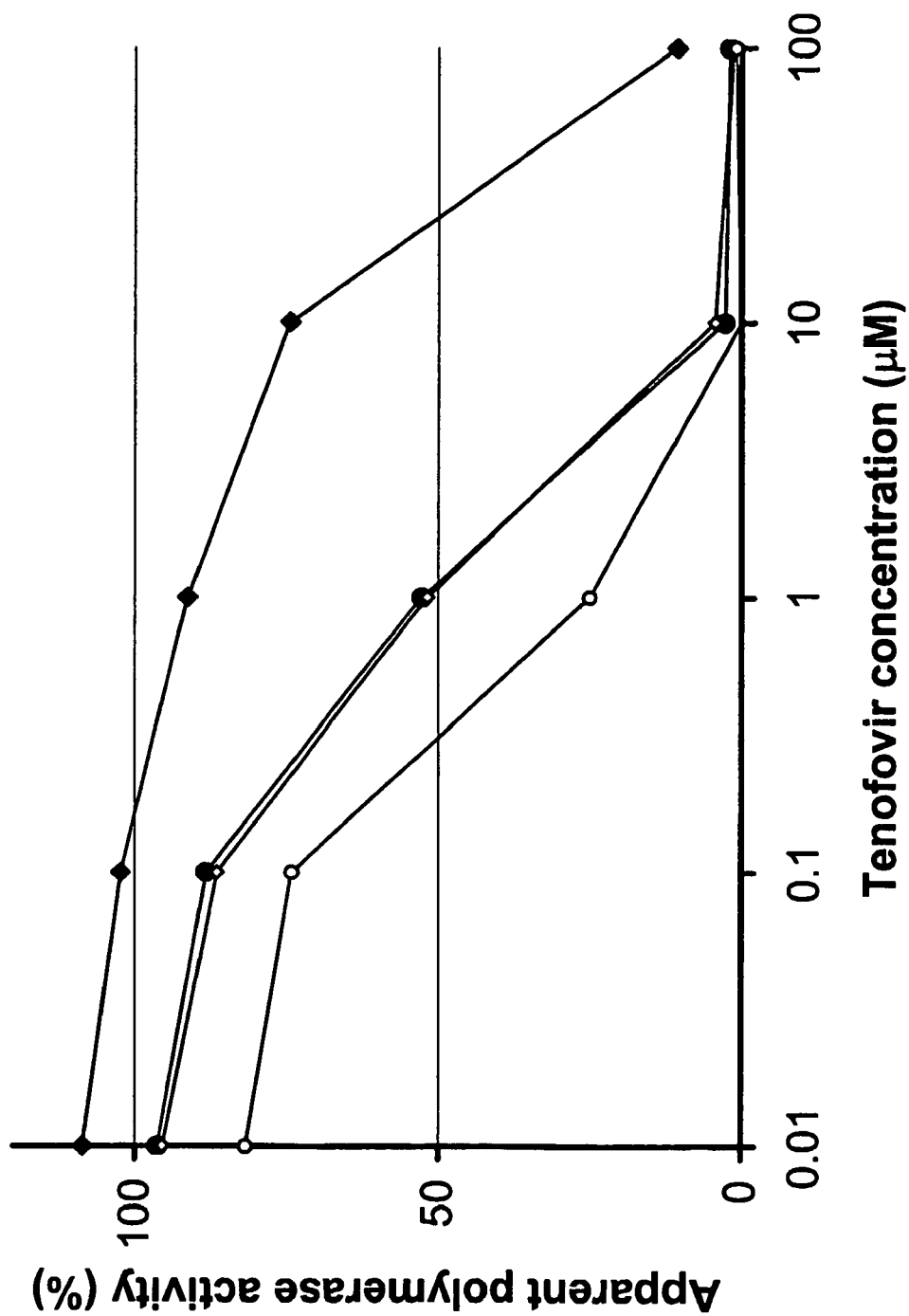

FIG. 4. shows that the biochemical mechanism underlying resistance to the antiviral drug tenofovir is based on enhancement of an ATP dependent phosphorolysis reaction. Symbols: HIV-1 wild type RT in standard reaction solution (○). HIV-1 wild type RT in reaction solution with ATP (●), HIV-1 mutant RT in standard reaction solution (◇), HIV-1 mutant RT in reaction solution with ATP(♦).

Figure 5:
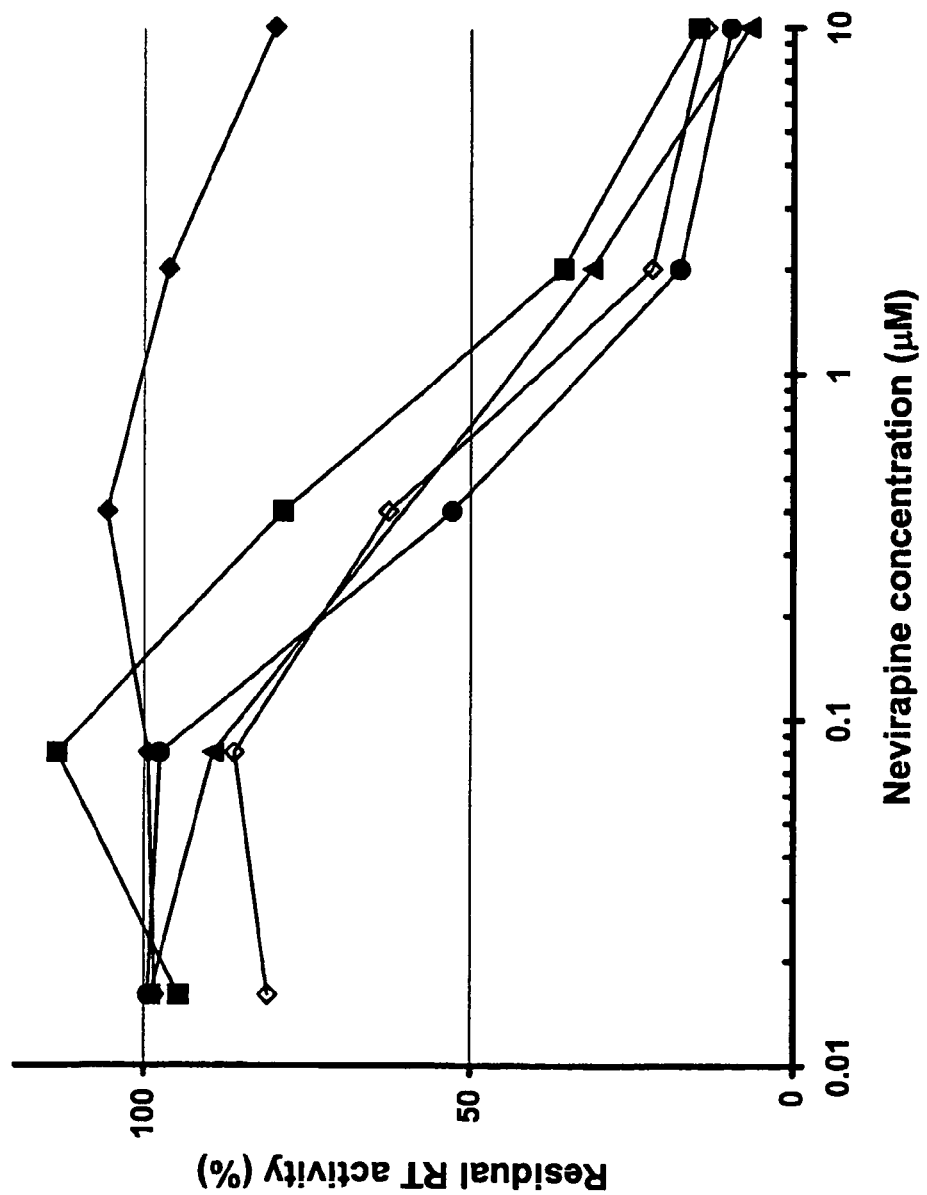

FIG. 5. exemplifies determination of susceptibility to the antiviral drug Nevirapine using RTs isolated from plasma from HIV infected individuals. Symbols: (□), (■) and (▲) RTs from infected individuals (●) a control consisting of recombinant HIV-1 wild type RT, (♦) a control consisting of mutated (L100I) recombinant HIV-1 RT with intermediate Nevirapine resistance.

DESCRIPTION OF EMBODIMENTS

Production of Primer Coated Microtiter Plates 1-ethyl-3-(3-dimethylamino-propyl)carboimide hydrochloride (final concentration 10 mg/ml) was added to a 100 mM 1-Methylimidazole buffer (pH 7.0) and the mixture was used to dilute the primer construct to a final concentration of 1 µg/ml. 100 µl of the primer solution was aliquoted to each well of a microtiter plate consisting of Nalge Nunc NucleoLink® transparent strips (Cat no 248259). The plates were incubated 6-8 hours at 37° C., washed thoroughly in 2M NaOH with 2 mM Ethylenediaminetetraacetic acid (EDTA) and soaked in three 5 L vials with water. Residual fluid in the wells was removed by tapping the plates upside down on absorbing cloth or paper. The plates were allowed to dry for 30 min at room temperature and finally frozen for storage at −20° C.

Protocol for DNA-Polymerase Assay.

The DNA-polymerase assay is based on a short primer with a specific sequence that is covalently bound to the wells of a 96 well microtiter plate. The reaction mixture contains a single stranded deoxynucleotide template with a part of the sequence complementary to the primer and the four deoxynucleoside triphosphates. Thymidine triphosphate is, however, replaced by 5-bromodeoxyuridine 5'-triphosphate (BrdUTP). The amount of bromodeoxyuridine monophosphate (BrdUMP) incorporated into DNA during the polymerase reaction, is detected with an alkaline phosphatase (Ap) conjugated anti-BrdU monoclonal antibody. An Ap substrate, 4-methylumbelliferyl phosphate, is used for fluorimetric product detection.

100 µl of DNA polymerase reaction mixture was added to each well of the primer coated microtiter plates. The samples were diluted in DNA polymerase base buffer and the polymerase reaction was initiated by transferring 50 µl sample dilution to each well on the plate. The microtiter plate was incubated at 33° C. and reaction was terminated after indicated times by washing the plate in 3 mM borate buffer (pH 8.9) with 1.5% (v/v)octophenoxypolyethoxyethanol (Triton X-100). Usually two incubation times, 4 hours and over night (16 hours), were used to check the linearity of the polymerization reaction. The plates were washed thoroughly in 2M NaOH with 2 mM EDTA and soaked in three 5 L vials with water.

Next the plates were incubated for 90 minutes at 33° C. with 100 µl alkaline phosphatase (Ap) conjugated anti-BrdU monoclonal antibody diluted to 4.8 µg/ml in 25 mM (bis[2-Hydroxyethyl]iminotris[hydroxymethyl]methane; 2-bis[2-Hydroxyethyl]amino-2-[hydroxymethyl]-1,3-propanediol) (Bis Tris) buffer (pH 7.2) with 50 mM NaCl, 37.5 mM $(NH_4)_2SO_4$, 1 mg/ml Dextran sulphate, 1% TritonX-100 and 25 mg/ml Sigma non-fat dried milk.

The plates were thereafter washed again in 3 mM borate buffer (pH 8.9) with 1.5% (v/v) TritonX-100 to remove unbound labeled antibody. The alkaline phosphatase activity was determined using 4-methylumbelliferyl phosphate substrate dissolved in Tris-buffer (pH 8.9). Fluorescence was read at 460 nm with a Wallac Victor 2 reader at defined intervals (excitation 355 mm).

Protocol for Determination of Inhibition of Second Strand Synthesis on Variable DNA Template.

The inhibition studies were performed in a modified DNA polymerase assay. The drugs were serially diluted in five steps and 25 µl aliquots were transferred to each well in the microtiter plate, mixed with 100 µl DNA polymerase reaction mixture and the enzyme reaction was initiated by addition of 25 µl enzyme dilution. Non-nucleoside analogues were studied at standard reaction conditions while the concentration of all four deoxynucleoside triphosphates (dNTP) were reduced to 1 µM in the studies of dNTP competing inhibitors. The polymerase reaction was allowed to proceed over-night (16-24 hours at 33° C.). Thereafter the reaction was terminated by a wash of the plate. The $IC_{50}$ value was defined as the concentration of drug giving 50% inhibition of the polymerase activity studied.

Protocol for Determination of RT Activity.

A modification of the calorimetric RT assay (Cavidi® Lenti RT activity kit), available from Cavidi Tech, Uppsala, Sweden was used for the determination of the level of RT activity in the virus preparations studied. The method has been described (Ekstrand at al 1996). In short, poly(rA) covalently bound to the wells of a 96 well microtiter plate serves as template for the incorporation of 5-bromodeoxyuridine 5'-triphosphate (BrdUTP) during the reverse transcription step at 33° C. The amount of bromodeoxyuridine monophosphate (BrdUMP) incorporated into DNA, is detected with an alkaline phosphatase (Ap) conjugated anti-BrdU monoclonal antibody. An Ap substrate, 4-methylumbelliferyl phosphate, is finally used for fluorimetric detection.

Protocol for Determination of Inhibition of Reverse Transcription.

The inhibition studies were performed in a modified Cavidi HS-kit Lenti RT assay. The inhibitors were serially diluted in five steps and 25 µl aliquots were transferred to each well in the microtiter plate, mixed with 100 µl RT reaction mixture and the enzyme reaction was initiated by addition of 50 µl enzyme dilution. The final nucleoside triphosphate substrate (BrdUTP) concentration was 16 µM he primer ($odT_{22}$) amount 12 ng per well. The RT reaction was allowed to proceed overnight (16-24 hours at 33° C. Thereafter the reaction was terminated by a wash of the plate. The $IC_{50}$ value was defined as the concentration of drug giving 50% inhibition of the RT activity studied.

Protocol for Isolation of Viral RT from Material which Contains RT Blocking Antibodies, Based on Destruction of Soluble Cellular Enzymes Followed by Isolation of Viral RT from Mini Columns.

1) Label the 4.5 ml plastic tubes to be used. Place them in a Nalgene box. Add 1 ml of sample (e.g. EDTA plasma from HIV infected individuals) to each labeled tube. Add 100 µl of a 66 mM solution of 5,5'-dithiobis-(2-nitrobenzoic acid) in buffered water, vortex and incubate the samples for one hour at room temperature.

The activity of the free plasma enzymes is destroyed during this procedure while the enzymes contained within the virions remain intact. The virions can then be purified from 5,5'-dithiobis-(2-nitrobenzoic acid), enzyme activity blocking antibodies and other substances that may interfere with quantification of viral RT by several separation procedures. The protocol below is based on the use of Fractogel® EMD TMAE Hicap gel.

2) Suspend the separation gel carefully and transfer 1500 µl gel slurry to each sample pre-treatment tube.

3) Incubate the samples with the gel slurry for 90 minutes at room temperature with the tubes lying down horizontally on an orbital shaker.

4) Label the desired amount of 10 ml plastic mini columns to identify the samples being analyzed. Mount the columns in a column washing device i.e. a Supelco Visiprep solid phase extraction vacuum manifold. Transfer the contents in the binding tubes to their corresponding columns. Before transfer vortex the tube briefly to evenly distribute the gel.

5) When all the columns are filled, apply the vacuum and suck the gels dry. Turn off the vacuum and start the washing by filling each column with 9 ml buffer A. When all columns have been filled, apply the vacuum and suck the gels dry.

6) Repeat step 5 three more times, giving a total of four washes. Suck the gels dry after each wash. After sucking the gels dry after the fourth wash, turn off the vacuum and proceed to step 7. The washing step removes unbound RT blocking antibodies and 5,5'-dithiobis-(2-nitrobenzoic acid) from the system.

7) Add to all dry gels 9 ml of conditioning buffer (B). After one minute apply vacuum and suck the gels dry.
8) Repeat step 7. Before turning off the vacuum check that all conditioning buffer (B) has been removed from all gels.
9) Lift off the upper part of the column wash device. Mount the tube holder with the labeled tubes into a clean container. Refit the upper part of the device. Control that the small tubings from each column go down in their corresponding tubes.
10) Add 600 µl lysis buffer (C) to each column. Let the buffer stand in the column for five minutes. Then apply the vacuum slowly and suck the gels dry. This will in each tube give approximately 600 µl of virus lysate from the connected gel.

The RT activity recovered in the lysates from step 10 are essentially free from RT blocking antibodies, drugs and cellular polymerase activity, and can be quantified with a sensitive RT activity assay, i.e. the Cavidi HS-kit Lenti RT, which is based on the method described by Ekstrand et al [7]. 25 µl lysate obtained according to the current protocol is sufficient for determination of the RT activity in the sample. The Remaining 575 µl sample should be frozen at −70° C. below for later use in the drug sensitivity test.

Note: RT enzymes that are not sensitive to cystein modifying agents e.g. wild type HIV 1 RT can optionally be assayed in the presence of up to 5 mM 5,5'-dithiobis-(2-nitrobenzoic acid). Sensitive enzymes such as MULV RT and RT from certain therapy resistant HIV 1 strains (containing e.g. the mutation Y181C) on the other hand require addition of a sulfhydryl reducing agent i.e. cystein or cysteamine to the lysis buffer.

Materials

Primer/Template for DNA Polymerase Assay.

The primer sequence is 18 bases 5'-GTC-CCT-GTT-CCG-GCG-CCA-3'(SEQ ID NO: 12) and linked at the 5' end to a primary amine by a C6 spacer arm.

The template construct contains three parts with different functions. From the 5' end: A (A)n polymer used to amplify the BrdU signal, a variable part (CTGA)m to obtain a polymerase reaction that is dependant on the four deoxynucleoside triphosphates and a sequence complementary to the primer.

In the experiments included in the examples n=12 and m=5, if not otherwise is stated.

Nucleosides, Enzyme Inhibitors and Antiviral Drugs ddATP, 2'3' dideoxyadenosine triphosphate; ddGTP, 2'3' dideoxyguanosine triphosphate;
ddCTP, 2'3' dideoxy cytidine triphosphate; ddTTP, 2'3' dideoxy thymidine triphosphate.
TMAU, 6-([3,4-trimethylene]anilino)uracil
Tenofovir, (R)-9-(2-phosphonylmethoxy-propyl)adenine; Nevirapine, (11-cyclopropyl-5,11-dihydro-4-methyl-6H-dipyrido[3,2-b:2',3'-f][1,4]diazepin-6-one) (NVP); and Efavirenz, (-)6-chloro-4-cyclopropylethynyl-4-trifluoromethyl-1,4-dihydro-2H-3,1-benzoxazin-2-one) (EFV).

Enzymes

DNA polymerase I (*E. coli*) was purchased from Amersham Bioscience. Recombinant DNA polymerase III from *Staphylococus aureus* was produced as described (Brown et al 1998). Mammalian DNA polymerase α (calf thymus) and β (human) were purchased from CHIMERx (Milwaukee). DNA polymerase γ was purified from beef heart as described (Pileur et al 2000).

NNRTI resistant mutant forms of HIV-1 RT were produced (L100I, K103N, L100I/K103N, Y181C). As template for the mutations was used the pETRT expression vector, which was constructed from the BH10 isolate. Mutations were generated using commercial site-directed mutagenesis kits, QuikChange (Stratagene). The mutations were verified by DNA sequence analysis. The mutated and native forms of RT were isolated as previously described (Lindberg et al 2002).

The procedure for production of recombinant HIV-1 RTs with AZT specific mutations were similar but the mutations were introduced into the RT-coding region from the HXB2-D isolate.

Plasma Samples from HIV Infected Individuals.

Plasma samples from treatment naïve patients or from patients treated with ordinary combination therapy were selected retrospectively. The amount of HIV-1 RNA in each sample was measured by standard HIV 1 RNA PCR (Cobas, Roche Diagnostica). Serum samples from patients with lympho proliferative disorders were obtained from the Department of Internal Medicine, Uppsala University, Akademiska sjukhuset, Uppsala Separation gel: e.g. Fractogel® EMD TMAE or Fractogel® EMD TMAE Hicap in 314 mM (2-(N-Morpholino)ethanesulfonic acid) (MES) pH 5.1, 413 mM Potassium iodide and Heparin 0.5 mg/ml.
Mini columns, e.g. Biorad Poly-Prep® (7311553)
Mini column washing device, i.e. Supelco Visiprep solid phase extraction vacuum manifold.
Plastic tubes, e.g. Nunc 4.5 ml cryogenic tubes.
Microtiter plates with immobilised prA, i.e. Nalge Nunc NucleoLinck®
Cysteine modifying agent, e.g. 66 mM 5,5'-dithiobis-(2-nitrobenzoic acid) in water buffered with 0.87 M Tris(hydroxymethyl)aminomethane (pH 8.3).
Mild sulfhydryl reducing agent, e.g. 33 mM cysteamine in water.

Buffers Used:

A) Wash buffer: 20 mM MES pH 5.4, 500 mM Potassium acetate (KAc)
B) Conditioning buffer. An RT assay compatible buffer e.g. 50 mM (N-(2-Hydroxyethylpiperazine-N'-(2-ethanesulfonic acid) (Hepes) pH 7.6, KAc 25 mM, magnesium chloride ($MgCl_2$) 20 mM, EthyleneGlycol-bis(β-aminoethyl Ether) N,N,N',N'-Tetraacetic Acid (EGTA) 0.2 mM, spermine 2 mM and heat inactivated bovine serum albumin (BSA) 0.5 mg/ml.
C) Lysis buffer: An RT assay compatible buffer including a detergent e.g. 1.25% Polyoxyethylene 4 Lauryl Ether (Brij 30), 13 ng/ml $odT_{22}$ and the same components as in the conditioning buffer (B). A sulfhydryl reducing agent, i.e. 0.2 mM cysteamine is optionally added when processing viruses with RT that are sensitive to SH oxidation/modification.

RT Reaction Mixture:

(N-(2-Hydroxyethylpiperazine-N'-(2-ethanesulfonic acid) (Hepes) 11.7 mM pH 7.6, BrdUTP 28.3 µM, $odT_{22}$ 120 ng/ml, $MgCl_2$ 4 mM, dextrane sulphate 0.05 g/l, spermine 2 mM, Triton-X 100 0.5%(v/v), EthyleneGlycol-bis(β-aminoethyl Ether) N,N,N',N'-Tetraacetic Acid (EGTA) 0.2 mM and bovine serum albumin (BSA) 0.5 mg/ml.

DNA Polymerase γ and Retro DNA Polymerase Base Buffer.

Hepes 50 mM pH 8.0, MgCl$_2$ 8 mM, dextrane sulphate 1.5 μg/l, spermine 1 mM, Triton-X 100 0.5%(v/v), EGTA 0.2 mM, dithiothreitol (DTT) 1.5 mM and bovine serum albumin (BSA) 0.5 mg/ml.

DNA Polymerase III Base Buffer.

(2-(N-Morpholino)ethanesulfonic acid) (MES) 40 mM pH 6.8, Potassium acetate (KAc) 40 mM, MgCl$_2$ 10 mM, spermine 2 mM, polyoxyethylenesorbitan monolaureate (Tween 20) 0.5%(v/v), EDTA 0.1 mM, dithiothreitol 1 mM and bovine serum albumin (BSA) 50 μg/ml.

DNA Polymerase β Base Buffer.

3-[(1,1-dimethyl-2-hydroxyethyl)amino]-2-hydroxy-1-propanesulfonic acid (AMPSO) 20 mM pH 8.3, MgCl$_2$ 1 mM, Spermidine 3 mM, BSA 1 μg/ml, EDTA 10 μM, DTT 0.1 mM, Tween 20 0.01%.

DNA Polymerase Reaction Mixture.

DNA polymerase base buffer reinforced with 24 μM BrdUTP, 49.5 μM dGTP, 49.5 μM dATP, 49.5 μM dCTP and 500 ng template/ml.

Retro DNA Polymerase Reaction Mixture with ATP.

The DNA polymerase γ and Retro DNA polymerase reaction mixture was reinforced with 3.2 mM ATP and pH was adjusted to 7.1.

EXAMPLES

Example 1

Utilization of Different Templates for Second Strand Synthesis by HIV RT

Two step dilution series of indicated template constructs starting from 200 ng/ml were included in each well of microtiter plates with immobilized primer according to "Production of primer coated microtiter plates". 100 fg recombinant HIV 1 RT was added to each well and the duration of the RT reaction was 18 hours. The polymerase activity on each template was determined according to "Protocol for DNA-polymerase assay" using DNA polymerase γ and Retro DNA polymerase base buffer. 50 mM NaCl or alternatively 100 mM was used during the binding of anti-BrdU monoclonal antibody. The activities found were plotted towards concentration of template and the maximal signal achieved for each template type were calculated from the plateau value of respective graph.

The results are summarized in Table 1. A clear correlation was found between the length of the A-tail and maximal signal obtainable in the polymerase assay. The length of the A-tail did also affect the ability of the antibody used for product detection to bind at increased ionic strength.

Example 2

Effects of Template Sequence on Inhibition of DNA Polymerase III with TMAU 6-anilinouracils are selective inhibitors of DNA polymerase III from gram-positive bacteria. The anilinouracil molecule inhibits its polymerase III target by sequestering it into an inactive DNA-drug-protein complex (Tarantino et al 1990). The drug TMAU can be regarded as an analogue to GTP. The inhibitory capacity of indicated concentrations of TMAU towards 1.25 ng/well recombinant DNA polymerase III was determined according to "Protocol for determination of inhibition of second strand synthesis on variable DNA template" utilizing either (CTGA)6-A12 (SEQ ID NO: 10) (■) or (CTG)6-A3 (SEQ ID NO: 11) (▲) as template. The polymerase reaction time was one hour and the GTP concentration in the DNA polymerase III reaction mixture was reduced to 2.5 μM. The polymerase activities obtained on indicated template were recalculated into % of the activities found with the same polymerase incubated in absence of inhibitor.

The results are depicted in FIG. 1. This highly specific inhibitor exhibited varying inhibitory capacity depending on the sequence of the template used. The current invention provides a system were the DNA template used easily can be changed to account for the specific conditions required by the enzyme or inhibitor studied.

Example 3

Detection Sensitivity of the DNA Polymerase Assay

The activity of serial dilutions of HIV 1 wild type RT (♦), mammalian DNA polymerase β (●) and E. coli DNA polymerase I (▲) were measured according to "Protocol for DNA-polymerase assay" utilizing base buffers optimized for indicated enzyme. The polymerase reaction time used was overnight (18 hours). The results are depicted in FIG. 2. Each of the three enzyme preparations displayed a linear relationship between amount of enzyme used and amount of product recovered. The assay background was 3800 rfu/hour. Utilizing double background as cut-off value for significant signal detection it was possible to detect down to 1 nU HIV 1 wild type RT, 6 nU mamalian DNA polymerase β and 3 nU E. coli DNA polymerase I.

Example 4

The Activity of Five DNA Polymerases in Different Assay Systems

The activity of serial dilutions of DNA polymerase α, DNA polymerase β, DNA polymerase γ, serum from a patient suffering from non-Hodgkin's lymphoma and HIV-1 RT were measured according to "Protocol for DNA-polymerase assay" and "Protocol for determination of RT activity" using reaction solutions based on indicated polymerase base buffers. The polymerase reaction time used was 2 hours. The activities found were recalculated into % of the activity on variable DNA template at the optimal reaction conditions for each enzyme. The results are shown in Table 2. Each of the five enzyme preparations investigated had their individual preferences concerning optimal reaction conditions. DNA polymerase a and the human serum polymerase, however, displayed a similar pattern. Only HIV-1 RT and DNA polymerase γ gave a significant activity in the reverse transcriptase assay.

Example 5

Demonstration of the Ability of the DNA Polymerase Assay to Measure Inhibition by the Dideoxy Analogues to All the Four DNA Bases The inhibitory capacity of indicated concentrations of ddATP (■), ddGTT (♦), ddCTP (●) and ddTTP (▲) towards the activity of 80 fg recombinant wild type HIV 1 RT was determined according to "Protocol for determination of inhibition of second strand synthesis on variable DNA template".

The polymerase activity at each inhibitor concentration was recalculated into % of the activity of a control in absence of inhibitor. The results are depicted in FIG. 3.

The polymerase reaction utilizing the template $(CTGA)_6$-$A_{12}$ (SEQ ID NO: 10) was found sensitive to inhibition by the dideoxy analogues to all the four DNA bases. The $IC_{50}$ values found varied from 20 nM for ddCTP to 80 nM for ddATP.

Example 6

Comparison of the Effect of Non-Nucleoside Inhibitors on First and Second Strand DNA Synthesis by HIV 1 RT The effects of three non-nucleoside inhibitors on indicated recombinant HIV 1 RT were determined according to "Protocol for determination of inhibition of second strand synthesis on variable DNA template" using DNA polymerase γ and Retro DNA polymerase base buffer and "Protocol for determination of inhibition of reverse transcription" respectively. The duration of the polymerization reactions were 19 hours for the second strand synthesis on $(CTGA)_6$-$A_{12}$ (SEQ ID NO: 10) and 2 hours for the first strand synthesis on prA respectively. The RT activities obtained were recalculated into % of the activities found with the same RT incubated in absence of inhibitor.

The results are summarized in Table 3. Both assay systems had the capacity to distinguish between resistant (Y181C, V179D) and sensitive RT enzymes. The IC50 values for any of the inhibitors was not significantly affected of a five fold difference in the amount of enzyme used in any of the two assay systems. Further there was no significant difference between the IC50 values achieved by measuring inhibition of first or second strand DNA synthesis.

Example 7

Demonstration of the Biochemical Mechanism Underlying Resistance to the Antiviral Drug Tenofovir Prolonged therapy of HIV infected individuals with nucleoside analogues leads to the development of resistant virus. This process is associated with the gradual appearance of mutations in the viral pol gene. The effects of these substitutions at the enzymatic levels are complicated and include enhancement of a primitive DNA editing function. This reaction is nucleotide dependent and produces dinucleoside polyphosphate and an extendible DNA 3' end.

The effects of serial dilutions of tenofovir triphosphate on 4 pg/well of indicated recombinant HIV 1 RT were determined according to "Protocol for determination of inhibition of second strand synthesis on variable DNA template" utilizing standard reaction solution based on DNA polymerase γ and Retro DNA polymerase base buffer and the same reaction solution supplemented with ATP. The duration of the polymerization reactions was 19 hours. The RT activities obtained were recalculated into % of the activity of the same RT incubated in absence of inhibitor. FIG. 4 shows the results.

Symbols: HIV-1 wild type RT in standard DNA polymerase reaction solution (○). HIV-1 wild type RT in DNA polymerase reaction solution with ATP (●), T69S→SS/L210W/T215Y HIV-1 mutant RT in standard DNA polymerase reaction solution (◇), T69S→SS/L210W/T215Y HIV-1 mutant RT in DNA polymerase reaction solution with ATP(◆).

The results depicted in FIG. 4 demonstrate that the difference in drug susceptibility between wild type and mutant RT increased approximately 10 fold when a reaction solution with capacity to support an ATP dependent phosphorolysis reaction was used.

Example 8

Determination of the Susceptibility to Nevirapine Using Plasma Derived RT

One ml samples of plasma from 3 HIV infected individuals from Stockholm, Sweden were processed according to "Protocol for isolation of viral RT from material which contains RT blocking antibodies, based on destruction of soluble cellular enzymes followed by isolation of viral RT from mini columns." Each plasma RT and two control enzymes were titrated towards a set of serial dilutions of Nevirapine according to "Protocol for determination of inhibition of second strand synthesis on variable DNA template" using "DNA polymerase γ and Retro DNA polymerase base buffer". See FIG. 5.

Symbols: (□) RT from patient 1 having 140 000 genome copies/ml (■) RT from patient 2 having 180 000 genome copies/ml, (▲) RT from patient 3 having 390 000 genome copies/ml, (●) a control consisting of recombinant HIV-1 wild type RT, (◆) and a control consisting of the recombinant HIV-1 mutant RT (L100I), with intermediate Nevirapine resistance.

The IC50 values towards Nevirapine found for the patient RTs varied from 0.7 to 1.2 μM. To be compared with 0.5 μM for the control wild type RT and >10 μM for the mutant RT with intermediate Nevirapine resistance (L100I).

Example 9

Detection of a DNA Polymerase Activity in Serum from Patients with Lymphoproliferative Disorders Serum from four patients suffering from non-Hodgkin's lymphoma and from six healthy blood donors were serially diluted in DNA polymerase III base buffer. The polymerase activity at each dilution step were measured according to "Protocol for DNA-polymerase assay" using two and six hours polymerase reaction time.

The DNA polymerase activity/μl serum sample and hour polymerase assay was calculated at the dilution range were there was a linear relationship between the amount of product formed and the amount of plasma added to the assay (see table 4).

Each serum sample from the patients with non-Hodgkin's lymphoma contained individual amounts of DNA polymerase activity, with similar properties as DNA-polymerase α (see table 3). The amount of activity ranged from approximately 2 to 190 times the average value found among healthy blood donors.

TABLE 1

Utilization of different templates for second strand synthesis by HIV RT.

| Template used | Maximal signal* (rfu/hour) | Background (rfu/hour) | Signal at 100 mM NaCl[a] (% of maximal signal) | SEQ ID NO: |
|---|---|---|---|---|
| (CTGA)5 | 89444 | 1629 | 20 | SEQ ID NO: 1 |
| (CTGA)5-A | 63694 | 1958 | 25 | SEQ ID NO: 2 |
| (CTGA)5-AA | 184421 | 613 | 33 | SEQ ID NO: 3 |
| (CTGA)5-AAAA | 239688 | 2565 | 44 | SEQ ID NO: 4 |
| (CTGA)5-A8 | 198894 | 1544 | 58 | SEQ ID NO: 5 |

TABLE 1-continued

Utilization of different templates for second strand synthesis by HIV RT.

| Template used | Maximal signal* (rfu/hour) | Background (rfu/hour) | Signal at 100 mM NaCl[a] (% of maximal signal) | SEQ ID NO: |
|---|---|---|---|---|
| (CTGA)6 | 60627 | 1285 | 22 | SEQ ID NO: 6 |
| (CTGA)6-AAA | 83555 | 1009 | ND | SEQ ID NO: 7 |
| (CTGA)6-A5 | 119326 | 914 | ND | SEQ ID NO: 8 |
| (CTGA)6-A9 | 202668 | 963 | ND | SEQ ID NO: 9 |
| (CTGA)6-A12 | 226062 | 726 | ND | SEQ ID NO: 10 |
| (CTG)6-A3 | 124334 | 814 | ND | SEQ ID NO: 11 |

*Two step dilution series of indicated template starting from 200 ng/ml were included in each well of microtiter plates with immobilized primer. 100 fg recombinant HIV 1 RT was added to each well and the duration of the RT reaction was 18 hours. 50 mM was used during the binding of anti-BrdU monoclonal antibody. The activities found were plotted towards concentration of template and the maximal signal achieved for each template was calculated.
[a]RT reaction conditions and calculations was identical as in "maximal signal", but 100 mM NaCl was used during the antibody binding.

TABLE 2

Apparent activity of four mammalian DNA polymerases and HIV RT in different assay systems

| | Activity of DNA polymerase isozyme in indicated assay (% *) | | | | |
|---|---|---|---|---|---|
| Base buffer | DNA pol α | DNA pol β | DNA pol γ | serum DNAp | HIV RT |
| Pol III | 100 | 17 | 0 | 100 | 0 |
| DNA pol β | 40 | 100 | 5 | 30 | 33 |
| DNA pol γ[a] | 1 | 13 | 100 | 9 | 100 |
| prA/Lenti[b] | 0 | 0 | 10 | 0 | 2175 |

*% of activity on variable DNA template with optimal base buffer for indicated isozyme
[a]DNA polymerase γ and Retro DNA polymerase base buffer.
[b]Activity in RT assay with prA/odT as primer template.

TABLE 3

Comparison of the effect of non-nucleoside inhibitors on first and second strand DNA synthesis by HIV 1 RT.

| | RT enzyme | | IC$_{50}$ (μm) on template* | |
|---|---|---|---|---|
| Inhibitor | Type | amount (fg) | (CTGA)$_6$-A$_{12}$ | prA |
| Nevirapine | wt | 100 | 2.0 | 2.2 |
| | wt | 20 | 2.0 | 2.5 |
| | Y181C | 100 | >500 | 200 |
| | Y181C | 20 | >500 | 180 |
| | V179D | 100 | 8 | 7 |
| | V179D | 20 | 12 | 8 |
| Efavirenz | wt | 100 | 0.04 | 0.02 |
| | wt | 20 | 0.03 | 0.02 |
| | Y181C | 100 | 0.12 | 0.15 |
| | Y181C | 20 | 0.14 | 0.13 |
| | V179D | 100 | 0.5 | 0.7 |
| | V179D | 20 | 0.4 | 0.6 |
| Foscarnet | wt | 100 | 0.5 | 0.7 |
| | wt | 20 | 0.5 | 0.6 |

*The effects of three non-nucleoside inhibitors on indicated recombinant HIV 1 RT were determined according to "Protocol for determination of inhibition of second strand synthesis on variable DNA template" and "Protocol for determination of inhibition of reverse transcription" respectively. The duration of the polymerization reactions were 19 hours for the second strand synthesis on (CTGA)$_6$-A$_{12}$ (SEQ ID NO: 10) and 2 hours for the first strand synthesis on prA respectively. The RT activities obtained were recalculated into % of the activities found with the same RT incubated in absence of inhibitor.

TABLE 4

Detection of a DNA polymerase activity in serum from patients with lymphoproliferative disorders.

| Serum code | Serum origin | Polymerase activity (rfu/hour/μl serum/ hour polymerase reaction)) |
|---|---|---|
| T1 | NHL patient[a] | 158521 |
| T2 | NHL patient | 1305 |
| T3 | NHL patient | 3405 |
| T4 | NHL patient | 16619 |
| B1-B6 | Blood donors | 841 ± 180 |

[a]Patient suffering from non-Hodgkin's lymphoma.
* NS, not significant.

Serum from four patients suffering from non-Hodgkin's lymphoma and from six healthy blood donors were serially diluted in DNA polymerase III base buffer. The polymerase activity at each dilution step were measured according to "Protocol for DNA-polymerase assay". The DNA polymerase activities tabulated was calculated from the dilution range were there was a linear relationship between the amount of product formed and the amount of plasma added. The assay background 854 flu/h has been subtracted from all values.

REFERENCES

Aposhian H V, Kornberg A. J.Biol.Chem. 1962, 237, 519

Arion D, Kaushik N, McCormick S, Borkow G, Parniak M A. Phenotypic mechanism of HIV-1 resistance to 3'-azido-3'-deoxythymidine (AZT): increased polymerization processivity and enhanced sensitivity to pyrophosphate of the mutant viral reverse transcriptase. Biochemistry. 1998 Nov. 10;37(45):15908-17.

Barnes M H, Leo C J, Brown N C. DNA polymerase III of Gram-positive eubacteria is a zinc metalloprotein conserving an essential finger-like domain. Biochemistry. 1998 Nov. 3;37(44): 15254-60

Eberle J, Seibl R, Kessler, C, Konig, Bernhard B. Reagents and kits for determining polymerase activity. 1997 U.S. Pat. No. 5,635,350:

Ekstrand D H, Awad R J, Källander C F, Gronowitz J S. A sensitive assay for the quantification of reverse transcriptase activity based on the use of carrier-bound template and non-radioactive-product detection, with special reference to human-immunodeficiency-virus isolation. Biotechnol Appl Biochem. 1996 Apr.; 23 (Pt 2):95-105.

Goff, S. P. (1990) Retrovirus reverse transcriptase: Synthesis, Structure, and Function. Review. J Acquir Imm Defic Syndr 3: 817-831.

Gronowitz; J S, Källander, C F R Method of determining dTk isoenzyme activity and the use thereof. 1987 U.S. Pat. No. 4,637.977:

Meyer P R, Matsuura S E, Mian A M, So A G, Scott W A. Related Articles. A mechanism of AZT resistance: an increase in nucleotide-dependent primer unblocking by mutant HIV-1 reverse transcriptase. Mol Cell. 1999 Jul.;4 (1):35-43

Pileur F, Toulme J, Cazenave C. Eukaryotic ribonucleases HI and HII generate characteristic hydrolytic patterns on DNA-RNA hybrids: further evidence that mitochondrial RNase H is an RNase HII. Nucleic Acids Res. 2000 Sep. 15;28(18):3674-83

Seville M, West A B, Cull M G, McHenry C S. Fluorometric assay for DNA polymerases and reverse transcriptase. Biotechniques. 1996 Oct.;21(4):664, 666, 668, 670, 672.

Tarantino P M Jr, Zhi C, Wright G E, Brown N C. Related Inhibitors of DNA polymerase III as novel antimicrobial agents against gram-positive eubacteria. Antimicrob Agents Chemother. 1999 Aug.;43(8):1982-7.

Tveit H, Kristensen T. Fluorescence-based DNA polymerase assay. Anal Biochem. 2001 Feb. 1;289(1):96-8.

Vandamme A M, Van Vaerenbergh K, De Clercq E. Anti-human immunodeficiency virus drug combination strategies. Antivir Chem Chemother. 1998 May;9(3):187-203.

---

The invention claimed is:

1. A method for measuring DNA-dependent DNA polymerisation in a biological sample, comprising the steps of
    a) providing a primer with a single stranded short specific sequence, which is unable to base pair internally, bound to a solid phase,
    b) contacting the solid phase bound primer with a reaction mixture containing the four deoxynucleoside triphosphates, one of which is modified so that it is specifically recognized by a labeled antibody, a single stranded deoxynucleotide template construct composed of, from the 5' end, a (A)n polymer and a variable part (CTGA)m or (CTG)m, and a sequence complementary to the primer, and n is greater than zero and m is greater than zero, with the proviso that n may be zero when the template is (CTGA)m,
    c) adding a biological sample comprising the DNA polymerase to the mixture of b),
    d) allowing the polymerase reaction to proceed,
    e) incubating the immobilized reaction product resulting from d) with the labeled antibody,
    f) detecting the amount of bound labeled antibody with the aid of the label used, and
    g) measuring the amount of incorporated modified deoxynucleoside triphosphate, as a measure of the DNA polymerization, with the aid of the label of the bound antibody.

2. The method according to claim 1, wherein the DNA polymerase is a retrovirus reverse transcriptase (RT).

3. The method according to claim 2, wherein the retrovirus RT is human immunodeficiency virus (HIV) RT.

4. The method according to claim 3, wherein the modified deoxynucleoside triphosphate is 5-bromodeoxyuridine 5'-triphosphate (BrdUTP) and the labeled antibody is an alkaline phosphatase (Ap) conjugated anti-BrU monoclonal antibody.

5. The method according to claim 3, wherein the measured DNA polymerisation is used for drug susceptibility testing.

6. The method according to claim 2, wherein the modified deoxynucleoside triphosphate is 5-bromodeoxyuridine 5'-triphosphate (BrdUTP) and the labeled antibody is an alkaline phosphatase (Ap) conjugated anti-BrU monoclonal antibody.

7. The method according to claim 2, wherein the measured DNA polymerisation is used for drug susceptibility testing.

8. The method according to claim 1, wherein the modified deoxynucleoside triphosphate is 5-bromodeoxyuridine 5'-triphosphate (BrdUTP) and the labeled antibody is an alkaline phosphatase (Ap) conjugated anti-BrU monoclonal antibody.

9. The method according to claim 8, wherein the measured DNA polymerisation is used for drug susceptibility testing.

10. The method according to claim 1, wherein the measured DNA polymerisation is used for drug susceptibility testing.

11. Commercial package for measuring DNA-dependent DNA polymerisation in a biological sample comprising
    a) a primer with a single stranded short specific sequence, which is unable to base pair internally, bound to a solid phase,
    b) a single stranded deoxynucleotide template construct composed of, from the 5' end, a (A)n polymer and a variable part (CTGA)m or (CTG)m and a sequence complementary to the primer in a), and n is greater than zero and m is greater than zero, with the proviso that n may be zero when the template is (CTGA)m,
    c) the four deoxynucleoside triphosphates, one of which is modified so that it is specifically recognized by a labeled antibody, and
    d) the labeled antibody that recognizes the modified deoxynucleoside triphosphate in c).

12. Commercial package for measuring DNA-dependent DNA polymerisation according to claim 11, further comprising a retroviral reverse transcriptase (RT).

13. Commercial package for measuring DNA-dependent DNA polymerisation according to claim 12, wherein the retroviral RT is human immunodeficiency virus (HIV) RT.

14. Commercial package for measuring DNA-dependent DNA polymerisation according to claim 11, wherein one of the four deoxynucleoside triphosphates, is 5-bromodeoxyuridine 5'-triphosphate (BrdUTP) which is specifically recognized by the alkaline phosphatase (Ap) conjugated anti-BrU monoclonal antibody that recognizes BrdUTP.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: template

<400> SEQUENCE: 1
ctgactgact gactgactga                                                      20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: template

<400> SEQUENCE: 2
ctgactgact gactgactga a                                                    21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: template

<400> SEQUENCE: 3
ctgactgact gactgactga aa                                                   22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: template

<400> SEQUENCE: 4
ctgactgact gactgactga aaaa                                                 24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: template

<400> SEQUENCE: 5
```
ctgactgact gactgactga aaaaaaaa        28

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: template

<400> SEQUENCE: 6
ctgactgact gactgactga ctga        24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: template

<400> SEQUENCE: 7
ctgactgact gactgactga ctgaaaa        27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: template

<400> SEQUENCE: 8
ctgactgact gactgactga ctgaaaaaa        29

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: template

<400> SEQUENCE: 9
ctgactgact gactgactga ctgaaaaaaa aaa        33

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: template

<400> SEQUENCE: 10
ctgactgact gactgactga ctgaaaaaaa aaaaaa        36

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: template

<400> SEQUENCE: 11
ctgctgctgc tgctgctgaa a        21

<210> SEQ ID NO 12
<211> LENGTH: 18
<212> TYPE: DNA
<213> ORGANISM: Artificial Sequence

```
<220> FEATURE:
<223> OTHER INFORMATION: Description of Artificial Sequence: primer

<400> SEQUENCE: 12
gtccctgttc cggcgcca                                                         18
```